United States Patent [19]

Johnston

[11] 4,360,524
[45] Nov. 23, 1982

[54] ETHERS OF 6-HALO-4-HALOMETHYLPYRIDINES AND THEIR FUNGICIDAL COMPOSITIONS AND USE

[75] Inventor: Howard Johnston, Walnut Creek, Calif.

[73] Assignee: The Dow Chemical Company, Midland, Mich.

[21] Appl. No.: 297,587

[22] Filed: Aug. 31, 1981

[51] Int. Cl.³ .................. A01N 43/40; C07D 213/64
[52] U.S. Cl. .................................. 424/263; 546/283
[58] Field of Search ...................... 546/283; 424/263

[56] References Cited

U.S. PATENT DOCUMENTS

| | | | |
|---|---|---|---|
| 3,244,722 | 4/1966 | Johnston et al. | 546/303 |
| 3,317,542 | 5/1967 | Haszeldine et al. | 546/296 |
| 3,983,238 | 9/1976 | Moresawa et al. | 424/266 |
| 4,062,962 | 12/1977 | Noveroske | 424/263 |
| 4,143,144 | 3/1979 | Tobol et al. | 546/283 |

Primary Examiner—John M. Ford
Assistant Examiner—Bernard Dentz
Attorney, Agent, or Firm—S. Preston Jones; Ronald G. Brookens

[57] ABSTRACT

Compounds are prepared which correspond to the formula

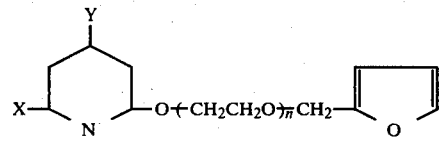

wherein Y represents trichloromethyl, dichloromethyl or dichlorofluoromethyl; X represents chloro, bromo or fluoro and n represents an integer of 1 or 2. These compounds and compositions containing them have been found to be useful as agronomic fungicides, especially useful and valuable for the control of soil-borne plant disease organisms which attack the roots of plants.

32 Claims, No Drawings

ETHERS OF 6-HALO-4-HALOMETHYLPYRIDINES AND THEIR FUNGICIDAL COMPOSITIONS AND USE

DESCRIPTION OF THE PRIOR ART

In U.S. Pat. No. 3,244,722, issued Apr. 5, 1966, there are described and claimed, among other related compounds, those corresponding to the formula

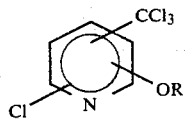

wherein R is alkyl of 1 to 18 carbon atoms or lower alkenyl. As reported in this patent, various compounds disclosed therein are useful as herbicides; various other compounds are useful in the control of pest fish and aquatic insects; and other compounds are taught to be useful as insecticides and anthelmintic agents for warm-blooded animals.

In U.S. Pat. No. 4,062,962, issued Dec. 13, 1977, a select group of the compounds taught in U.S. Pat. No. 3,244,722 are taught as fungicides for the control of soil-borne plant disease organisms which attack the roots of plants.

In U.S. Pat. No. 3,983,238, issued Sept. 28, 1976, there are described and claimed compounds having anticoccidioidal activity. These compounds are of the formula:

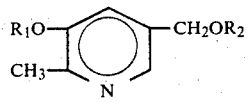

wherein $R_1$ and $R_2$ are each hydrogen, aliphatic acyl, aromatic acyl or heterocyclic acyl with at least $R_1$ or $R_2$ being heterocyclic acyl.

In U.S. Pat. No. 4,143,144, issued Mar. 6, 1979, there are described and claimed antifungal compounds of the formula

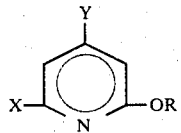

wherein Y is trichloromethyl, dichloromethyl or dichlorofluoromethyl; X represents chloro, bromo, fluoro, $C_1$–$C_4$ alkoxy or OR; R represents

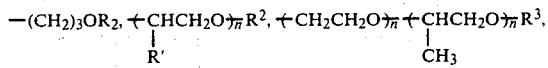

5-substituted-2-furanylmethyl, tetrahydro-3-furyl, tetrahydro-2-furylmethyl, tetrahydro-2-pyranylmethyl, 2-thiophenemethyl, 2,3-dihydrobenzodioxin-2-ylmethyl or 2,2-dimethyl-1,3-dioxolan-4-ylmethyl; each R' independently represents H or $CH_3$; $R^2$ represents H, $C_1$–$C_4$ alkyl or phenyl; $R^3$ represents H or $C_1$–$C_4$ alkyl and each n independently represents an integer of from 1 to 12.

Other related art includes U.S. Pat. No. 3,317,542, issued May 2, 1967, which is directed to compounds of the formula

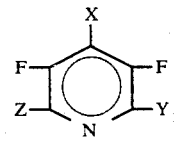

wherein X, Y and Z may be the same or different and each represents a list of groups including alkoxy and methyl. The utility of these compounds is not set forth.

SUMMARY OF THE INVENTION

The present invention is directed to compounds corresponding to the formula

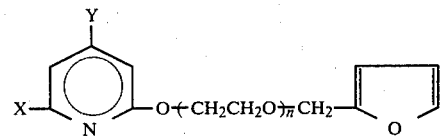

In this and succeeding formulae, Y represents trichloromethyl, dichloromethyl or dichlorofluoromethyl; X represents chloro, bromo or fluoro and n represents an integer of 1 or 2.

The pyridine compounds of the present invention are crystalline solids or oils and are of low solubility in water and of moderate solubility in common organic solvents.

The pyridine compounds of the present invention and compositions containing said compounds have been found useful, as agronomic fungicides, especially useful and valuable for the control of soil-borne plant root disease organisms.

The compounds of the present invention can be prepared by a variety of methods. In the preparation of compounds wherein X is chloro, bromo or fluoro, the compounds can be prepared by the reaction of an appropriate halomethyl substituted dihalopyridine reactant with an alkali metal salt of the appropriate 2-furanylmethoxyethanol or 2-furanylmethoxyethoxyethanol in the presence of a reaction medium (the alkali metal salt can be preformed or formed in situ). This reaction can be represented as follows:

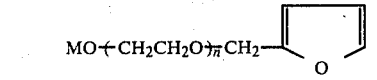

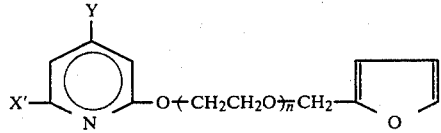

In the above reaction representation, no attempt has been made to present a balanced equation. In addition, X' represents chloro, bromo or fluoro; Y and X are as hereinbefore defined and M represents sodium, potassium, lithium, or cesium.

In carrying out the above reaction, the appropriate halomethyl substituted dihalopyridine reactant is mixed with the alkali metal salt of the appropriate 2-furanylmethoxyethanol or 2-furanylmethoxyethoxyethanol reactant and the reaction medium and the mixture heated between about 40° and about 70° C. until the reaction is complete. The reaction is usually complete in from about 0.5 to about 5.0 hours, depending upon the specific reactants and solvents employed.

After the completion of the reaction, the reaction mixture is usually diluted with water and extracted with a solvent such as methylene chloride, petroleum ether, hexane or toluene. The extract is thereafter usually washed with water, dried, and filtered, if desired, and the solvent and any residual alcoholic by-products present are removed by evaporation or other conventional separatory procedures. The product is thereafter recovered and, if desired, can be further purified by various conventional techniques such as crystallization and/or recrystallization from solvents such as, for example, methanol, hexane or toluene or by distillation depending upon whether the product is a solid or oil.

In carrying out the above preparations, the amounts of the reactants employed are not critical as some of the desired product is formed with any amounts. However, since the reaction consumes the reactants in equimolar proportions (1 molar equivalent of the alkali metal salt reactant for the halogen atom to be reacted), these amounts for the most part should be employed. It has, however, been found that an increase in the yield of the desired product can be obtained by employing a slight excess of the alkali metal salt reactant. Therefore, it is preferred to employ from about 1.0 to about 1.5 molar equivalents of the alkali metal salt reactant for the halogen atom to be reacted.

Representative reaction medias useful for carrying out the above preparations include, for example, dimethylsulfoxide, dimethylformamide or toluene.

PREPARATION OF STARTING MATERIALS 2,6-Dichloro-4-(dichloromethyl)pyridine

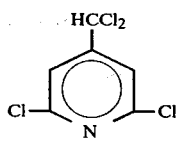

To a solution of 73 grams (0.275 mole) of 2,6-dichloro-4-(trichloromethyl)pyridine dissolved in 125 milliliters of acetone was added a solution of 108 grams (0.48 mole) of stannous chloride hydrate and 40 milliliters of concentrated hydrochloric acid in 500 milliliters of acetone. The mixture was refluxed for 2.0 hours. The solid which formed was separated by filtration and three fourths of the solvent was thereafter removed by evaporation. The remainder of the reaction mixture was diluted with water and the oil phase which formed, removed by extraction with hexane. The 2,6-dichloro-4-(dichloromethyl)pyridine product was dried and recovered from the solvent by evaporation of the solvent. The product has a boiling point of 123°-126° C. at 1.6 millimeters of mercury.

2,6-Dichloro-4-(dichlorofluoromethyl)pyridine

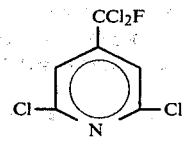

A mixture containing 138.5 grams (0.522 mole) of 2,6-dichloro-4-(trichloromethyl)pyridine and 34 grams (0.187 mole) of antimony trifluoride was heated to 80°-84° C. and maintained under agitation for 23 minutes. During this step, a slow stream for chlorine gas was passed over the surface of the reaction mixture. The reaction mixture was steam distilled and the crude 2,6-dichloro-4-(dichlorofluoromethyl)pyridine was purified by fractionation. The product had a boiling point of 74°-76° C. at 1.0 millimeter of mercury.

The 2,6-dibromo and difluoro counterparts of the above dichloro compounds can be prepared by conventional halogen exchange. They can also be prepared by employing the 2,6-dibromo(or difluoro)-4-(trichloromethyl)pyridine as the starting material in the above procedure.

The compounds employed as starting materials of the present invention which correspond to the formula:

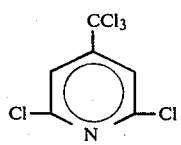

can be prepared as taught in U.S. Pat. No. 3,244,722. This patent teaches that the compounds may be prepared by contacting an appropriate methylpyridine and hydrogen chloride at temperatures of about 50° C. to produce a liquid methylpyridine hydrochloride composition, thereafter passing chlorine gas through the liquid mixture at temperatures of from about 95° to about 110° C. while irradiating the reaction mixture and thereafter fractionally distilling the liquid mixture. The compounds may also be prepared by rapidly mixing in the vapor phase chlorine, an appropriate methylpyridine and an inert diluent such as perchlorinated hydrocarbon during a brief contact time at temperatures of from about 400° C. to about 490° C. and thereafter cooling to precipitate the desired starting material or fractionally distilling to recover the desired starting material.

The compounds employed as starting materials which correspond to the formula:

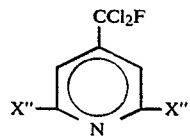

wherein each X'' is chloro, bromo or fluoro can also be prepared employing the procedures taught by McBee et al., 2nd Eng. Chem. 39, pages 389–391 (1947) (see Chem. Abstracts, Vol. 41, page 3461d). In this procedure an appropriate 2,6-dihalo-4-(trichloromethyl)pyridine is treated with HF in an autoclave at temperatures up to 300° C.

It should be further noted that while there are many procedures for preparing the above starting materials, they all can be prepared employing the procedures outlined in U.S. Pat. No. 3,244,722 or modifications thereof or combinations of any of the procedures outlined hereinabove.

The 2-furanylmethoxyethanol and the 2-(furanylmethoxy)ethoxyethanol starting materials can be prepared by reacting furfuryl alcohol with 1 or 2 moles of ethylene oxide, respectively, employing conventional reaction procedures.

The compounds of the present invention and formulation containing them have been found to be useful as agronomic fungicides, especially valuable for the control of soil-borne plant root disease organisms which attack the roots of plants. In accordance with the present invention, a method for protecting plants, which are in soil containing soil-borne plant root disease organisms, from attack by said organisms, is provided, which comprises contacting plants or plant parts with a non-phytotoxic plant protecting amount of at least one of the compound set forth hereinabove or with a composition (formulation) containing at least one of the compounds.

One of the advantages of the present method is that by the mode of action of the active toxicant, plant root diseases can be eliminated from infected plants and non-infected plants can be protected from attack.

The present method also offers a practical advantage in that there is no need to employ the additional time and labor required by conventional pre-plant sterilization with soil fumigants.

A further practical advantage of the present method is that the active compounds or toxicants are used in amounts which are the equivalent of ounces of the active ingredient on a per acre basis as against the conventional soil fumigation practices which require pounds and hundreds of pounds of active material per acre.

In the present specification and claims, the term "plant part" is employed to designate all parts of a plant and includes seeds, the underground portion, i.e., bulbs, stolons, tubers, rhizomes, ratoons, corms, the root system, hereinafter commonly referred to as root, and the above-ground portion, i.e., the crown, stalk, stem, foliage or leaf system, fruit or flower.

In the present specification and claims, the term "systemic" defines the translocation of the active compound employed in the present method through the plant whereby they selectively accumulate principally in the underground portions of the plant. The following illustrative example will further the understanding of the term "systemic" as used herein. If the active compounds are applied to seeds, accumulation of the active compound is found mainly in the underground system of the germinating seed; if applied to storage organs (bulbs, stolons, tubers, rhizomes, ratoons or corms), the active compound will absorb into the plant tissue and upon active growth following dormancy, the compound will be found mainly in the below-ground portion of the growing plant; if applied to the above-ground portions of the plant, the active compounds downwardly translocate and principally accumulate in the underground system; and application of the active compound adjacent the underground portions of the plant gives remarkably fast protection by the compound, due to the proximity of the point of application to the area of chemical accumulation, and to the fact there is mainly no translocation away from the underground system.

Compositions containing one or more of the active compounds of the present invention have been found to be very effective in the control of plant root disease in plants either before or after the plant has been attacked by soil-borne plant root disease organisms.

Representative soil-borne plant root disease organisms which attack the below-ground portion of plants, i.e., the root system and which are controlled by the present method include Verticillium, Fusarium, Rhizoctonia, Phytophthora, Pythium, Thielaviopsis, Aphanomyces and gram-negative bacteria such as Pseudomonas.

Control of soil-borne plant disease by the present invention is achieved, for example, in cereal crops such as corn, wheat, barley, rye, oats, rice and sorghum; vegetable crops such as tomatoes, peppers, lettuce, onions, cabbage, broccoli, squash, cucumbers, cauliflower, etc.; legumes such as peanuts, soybeans, beans, peas and alfalfa; root crops such as turnips, beets, carrots, white potatoes, sweet potatoes and yams; fiber crops such as cotton, flax and hemp; fruit crops such as apples, bananas, cantaloupes, cherries, dates, figs, grapes, pineapples, grapefruit, lemons, limes, oranges, peaches, pears, plums, strawberries and watermelon; oil crops such as castorbean, copra, olives, palms, rubber and sunflower; stimulants such as cocoa, coffee, tea and tobacco; sugar crops such as sugar cane and sugar beets; turf including bent grass and blue grass, rye and fescue; ornamentals such as chrysanthemums, zinnias, carnations, lilies, violets, petunias, marigolds, philodendrons, schefflera, dracaena, wax plants, jade plant, ivy, ferns, rubber plants, cactus and dieffenbachia; woody ornamentals such as pines, roses, rhododendrons, azaleas, boxwoods, spruces and the like. While the above lists a variety of crop plants which may be treated by the practice of the present invention, it is to be understood that the present method is not restricted to the above list of crop plants.

Generally in the actual practice of the method of the present invention, a plant protecting amount of the active toxicant compounds can be applied to the plant or plant part by a variety of convenient procedures. Such procedures include soil incorporation whereby compositions containing the active toxicant are mechanically mixed with the soil; applied to the surface of the soil and thereafter dragged, disced or rototilled into the soil; or transported into the soil with a liquid carrier such as by injection, spraying or irrigation. Additionally, a plant protecting amount of the active toxicant compounds can be employed in sprays, gels or coatings for above-ground applications or drenched onto the soil surface. In additional application methods, the active toxicant can be applied by vapor transfer; added in liquid or solid composition to hydroponic operations; seed treatment operations and by conventional plant part coating operations or other techniques known to those skilled in the art. The only limitation upon the mode of application employed is that it must be one which will ultimately allow the toxicant to come in contact with plants or plant parts.

The exact dosage of the active toxicant employed can be varied depending upon the specific plant, its stage of development, hardiness, the mode of application and its growth media. Generally, the active ingredient should be present in an amount equivalent to from about 50 micrograms to about 140 grams or more per plant on a per plant basis. Translating this into conventional application rates, this amount is equivalent to from about 0.0005 pound to about 10 pounds or more of the active ingredient on a per acre basis, as chemical available to the plant.

It will be appreciated that on a per plant basis, seed treatment of small seeded plant species such as grasses, carrots, and the like will actually require much smaller amounts than 50 micrograms per plant. Generally, rates in the range of 1/32 to about 8 ounces per 100 pounds of seeds will be optimum for seed treatment among the diversity of plant species. For practices such as conventional tobacco transplant treatment or in-furrow soil treatment of plants such as soybeans at seeding and the like, an amount of active toxicant approximately equal to 8 to about 32 milligrams would be utilized on a per plant basis.

Larger amounts of the active ingredient may advantageously be applied when treatments are employed which distribute the material throughout the soil. For example, when the active ingredient is applied as an at-plant row treatment or an early or mid-season post-plant side dress treatment, those amounts of chemical not proximal to plant roots are essentially unavailable to the plant and therefore not effective as set forth hereinabove. In such practices, the amount of the active ingredient employed needs to be increased to rates as high as about 20 pounds per acre or higher to assure that the requisite effective quantity of active ingredient is made available to the plants.

The present invention can be carried out by employing the pyridine compounds directly, either singly or in combination. However, the present invention also embraces the employment of liquids, dusts, wettable powders, granules or encapsulated compositions containing at least one of said compounds as active ingredient. In such usage, the compound or compounds can be modified with one or more of a plurality of additaments or adjuvants including inert solvents, inert liquid carriers and/or surface active dispersing agents and coarsely or finely-divided inert solids. The augmented compositions are also adapted to be employed as concentrates and subsequently diluted with additional inert carrier to produce other compositions in the form of dusts, sprays, granules, washes or drenches. In compositions where the adjuvant is a coarsely or finely-divided solid, a surface active agent or the combination of a surface active agent and a liquid additament, the adjuvant cooperates with the active component so as to facilitate the invention. Whether the composition is employed in liquid, wettable powder, gel, wax, jelly, dust, granule or encapsulated form, the active compound will normally be present in an amount of from 2 to 98 percent by weight of the total composition.

In the preparation of dust, or wettable powder compositions, the toxicant products can be compounded with any of the finely-divided solids, such as pyrophyllite, talc, chalk, gypsum, fuller's earth, bentonite, attapulgite, modified clays, starch, casein, gluten and the like. In such operations, the finely-divided carrier is ground or mixed with the toxicant or wet with a solution of the toxicant in a volatile organic solvent. Also, such compositions when employed as concentrates can be dispersed in water, with or without the aid of dispersing agents to form spray mixtures.

Granular formulations are usually prepared by impregnating a solution of the toxicant in a volatile organic solvent onto a bed of coarsely divided attapulgite, bentonite, diatomite, organic carriers such as ground corn cobs, walnut hulls, or the like.

Similarly, the toxicant products can be compounded with a suitable water-immiscible inert organic liquid and a surface active dispersing agent to produce an emulsifiable concentrate which can be further diluted with water and oil to form spray mixtures in the form of oil-in-water emulsions. In such compositions, the carrier comprises an aqueous emulsion, i.e., a mixture of inert water-immiscible solvent, emulsifying agent and water. Preferred dispersing agents which can be employed in these compositions, are oil-soluble materials including non-ionic emulsifiers such as the condensation products of alkylene oxides with the inorganic acids, polyoxyethylene derivatives or sorbitan esters, complex ether alcohols, alkyl phenols and the like. Also, oil-soluble ionic emulsifying agents such as mahogany soaps can be used. Suitable inert organic liquids which can be employed in the compositions include petroleum oils and distillates, toluene, liquid halohydrocarbons, synthetic organic oils and vegetable oils. The surface-active dispersing agents are usually employed in liquid compositions and in the amount of from 0.1 to 20 percent by weight of the combined weight of the dispersing agent and active compound.

In addition, other liquid compositions containing the desired amount of effective agent can be prepared by dissolving the toxicant in an inert organic liquid such as acetone, methylene chloride, chlorobenzene and petroleum distillates. The preferred inert organic solvent carriers are those which are adapted to accomplish the penetration and impregnation of the environment and particularly soil with the toxicant compounds and are of such volatility as to leave little permanent residue thereon. Particularly desirable carriers are the petroleum distillates boiling almost entirely under 400° F. at atmospheric pressure and having a flash point above 80° F. Also desirable are those petroleum fractions with higher boiling points which can leave residues due to their low vapor pressure, provided they are low in aromatic content such as paraffinic and isoparaffinic oils which are of low phytotoxicity potential. The proportion of the compounds of this invention employed in a suitable solvent may vary from about 2 to about 50 percent or higher. Additionally, the active components can be compounded with water or petroleum jellies to prepare the viscous or semi-solid treating compositions.

The expression "soil" is employed herein in its broadest sense to be inclusive of all conventional "soils", as defined in Webster's New International Dictionary, Second Edition, unabridged, published in 1937, G. C. Merriam Co., Springfield, Mass. Thus, the term refers to any substance or medium in which plants may take root and grow, and is intended to include not only earth, but also compost, manure, muck, sand, synthetic growth mediums such as vermiculite and pearlite and the like, adapted to support plant growth. In this context, hydroponic growth mediums are also included.

DESCRIPTION OF SOME PREFERRED EMBODIMENTS FOR USE

In order that the method of the present invention may be more fully understood, the following examples are given to illustrate the manner by which the method can be practiced but, as such, should not be construed as limitations upon the overall scope of the same.

EXAMPLE I

Soil infested with the tobacco black shank pathogen *Phytophthora parasitica* var. nicotianeae was uniformly mixed and placed in 6-inch pots. To said pots were transplanted six week old tobacco seedlings of the "402" variety which had been grown in pathogen free soil. Test dispersions of 2-chloro-6-(2-(2-furanylmethoxy)ethoxy)-4-(trichloromethyl)pyridine were prepared by dissolving a predetermined amount of the chemical in a predetermined amount of acetone containing Tween 85 emulsifier (a proprietary material of Imperial Chemical Industries, U.S., which is a polyoxyethylene (20) sorbitan trioleate) and thereafter diluting the solution with water to prepare dispersions containing 50, 25, 12.5, 6.25 and 3.125 parts by weight of the compound per million parts of the ultimate dispersion. Thereafter, the test dispersions were employed to treat separate pots containing the seedlings by pouring 100 cubic centimeters of each of the dispersions onto the soil, assuring root contact with sufficient chemical. Additional pots were treated with an aqueous acetone/Tween 85 solution containing no toxicant to serve as controls. After treatments, the plants were maintained under conditions conducive for good plant growth. Three weeks after treatment, the plants were examined for disease control. The results of this examination are set forth below in Table I.

TABLE I

| Active Compound Employed | Application Rate in ppm | Percent Control Of *Phytophthora Parasitica* In Tobacco Seedlings 3 weeks |
|---|---|---|
| 2-chloro-6-(2-(2-furanyl-methoxy)ethoxy)-4-(trichloromethyl)pryidine | 50 | 100 |
|  | 25 | 100 |
|  | 12.5 | 100 |
|  | 6.25 | 100 |
|  | 3.125 | 100 |
| Acetone Control | — | 0 |

EXAMPLE II

Acetone dispersions were prepared by admixing predetermined amounts of 2-chloro-6-(2-(2-furanylmethoxy)ethoxy)-4-(trichloromethyl)pyridine with predetermined amounts of acetone, water and surfactant.

Soil infested with the soybean root rot disease organism *Phytophthora megasperma* was uniformly mixed and used to fill 3-inch pots. Five soybean seeds of the variety "Harosoy 63" were planted in each pot with 4 pots being used per test mixture. The pots were treated by spraying a predetermined amount of one of the test mixtures directly onto the soil surface and seeds in the pots to give dosages equivalent to 4.0, 2.0 and 1.0 ounce of the active compound per acre, applied as an in-furrow treatment, wherein a 1-inch band of a crop with a 30-inch row spacing is treated. After the acetone had evaporated, the soil in the pots was capped with a layer of sterile soil. Additional pots were also prepared as above to serve as controls and sprayed with no-toxicant containing acetone-water-surfactant solution. The pots were thereafter maintained under conditions conducive to both plant growth and disease development. Six, 14, 21 and 31 days after treatment, the pots were examined to determine the amount of disease control, as evidenced by the number of plants surviving. The results of the examination are set forth below in Table II.

TABLE II

| Compound | Equivalent Pounds per Acre in-furrow | Percent of Plants Surviving at Indicated Dosage and Number of Days After Planting | | | |
|---|---|---|---|---|---|
| | | 6 | 14 | 21 | 31 |
| 2-chloro-6-(2-(2-furanylmethoxy-ethoxy)-4-trichloromethyl)pyridine | 4.0 | 92 | 90 | 84 | 78 |
| | 2.0 | 92 | 84 | 66 | 62 |
| | 1.0 | 94 | 86 | 66 | 60 |
| Control | — | 98 | 70 | 50 | 38 |

EXAMPLE III

An acetone dispersion was prepared by admixing a predetermined amount of 2-chloro-6-(2-(2-furanylmethoxy)ethoxy)-4-(trichloromethyl)pyridine with a predetermined amount of acetone, water and surfactant.

Soil infested with the soybean root rot disease organism *Phytophthora megasperma* was uniformly mixed and used to fill 3-inch pots. Five soybean seeds of the variety "Harosoy 63" were planted in each pot with 4 pots being used per test mixture. The pots were treated by spraying a predetermined amount of one of the test mixtures directly onto the soil surface and seeds in the pots to give dosages equivalent to 1.0 pound of the active compound per acre applied as an in-furrow treatment, wherein a 1-inch band of a crop with a 30-inch row spacing is treated. After the acetone had evaporated, the soil in the pots was capped with a layer of sterile soil. Additional pots were also prepared as above to serve as controls and sprayed with a no-toxicant containing acetone-water-surfactant solution. The pots were thereafter maintained under conditions conducive to both plant growth and disease development. Six, 14, 21 and 31 days after treatment, the pots were examined to determine the amount of disease control, as evidenced by the number of plants surviving. The results of the examination are set forth below in Table III.

TABLE III

| Compound | Equivalent Pounds per Acre in-furrow | Percent of Plants Surviving at Indicated Dosage and Number of Days After Planting | | | |
|---|---|---|---|---|---|
| | | 6 | 14 | 21 | 31 |
| 2-chloro-6-(2-(2-furanylmethoxy)-ethoxy)-4-(trichloromethyl)pyridine | 1.0 | 90 | 90 | 80 | 80 |
| Control | — | 90 | 82 | 70 | 56 |

When applied as hereinabove set forth, each of the compounds of the present invention, the utility of which has not been specifically exemplified above, has the ability to kill and control one or more of the hereinabove listed fungal organism.

DESCRIPTION OF SOME PREFERRED EMBODIMENTS FOR COMPOUND PREPARATION

In order that the present invention can be more fully understood, the following examples are given primarily by way of illustration and should not be construed as limitations upon the overall scope of the same.

EXAMPLE IV

2-Chloro-6-(2-(2-furanylmethoxy)ethoxy)-4-(trichloromethyl)pyridine

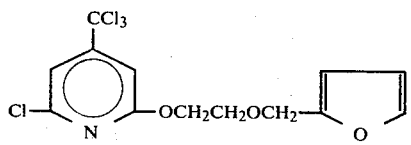

A mixture of 60 milliliters (Ml) of 2-furanylmethoxyethanol and 15 ml of water was placed in a 300 ml flat bottom flask equipped with a thermometer and stirrer. A solution of sodium hydroxide (4.8 grams (g), 0.12 mole) in 7.0 ml of water was then added and the resulting solution stirred for ~10 minutes while being warmed to 45° C.

To the above mixture, being vigorously stirred, was added, over a five-minute period, 21.2 g (0.08 mole) of 2,6-dichloro-4-(trichloromethyl)pyridine, which had been ground to a fine powder. Air in the flask was displaced with nitrogen gas before the addition was begun. When the addition was completed, the thus formed solution was warmed from 45° to 70° C. of a 1 hour period and then held there for 1 hour. At the end of this time, the reaction product was poured into 550 ml of water and the mixture extracted with hexane. The extract was treated with decolorizing carbon and the hexane removed by evaporation under reduced pressure leaving the 2-chloro-6-(2-(2-furanylmethoxy)-ethoxy)-4-(trichloromethyl)pyridine product as an amber oil.

The product was recovered in a yield of 15 grams and had a refractive index of $\eta 25/D = 1.5588$. Upon analysis, the product was found to have carbon, hydrogen, nitrogen, and chlorine contents of 42.13, 3.00, 3.69, and 37.98 percent, respectively, as compared with the theoretical contents of 42.08, 2.99, 3.78 and 38.22 percent, respectively, as calculated for the above named structure.

By following the above preparative procedure, the following compounds are prepared

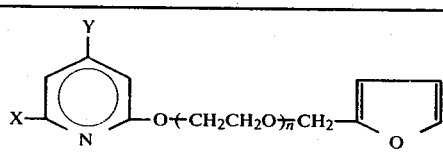

| X | Y | n |
|---|---|---|
| F/Br | CCl$_3$ | 2 |
| Cl/F/Br | CCl$_3$ | 1 |
| Cl/F/Br | CHCl$_2$ | 1 |
| Cl/F/Br | CHCl$_2$ | 2 |
| Cl/F/Br | CFCl$_2$ | 1 |
| Cl/F/Br | CFCl$_2$ | 2 |

What is claimed is:

1. A compound corresponding to the formula:

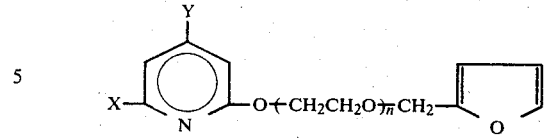

wherein Y represents trichloromethyl, dichloromethyl or dichlorofluoromethyl; X represents chloro, bromo, or fluoro and n represents an integer of 1 or 2.

2. A compound as defined in claim 1 wherein Y is trichloromethyl.

3. A compound as defined in claim 2 wherein X is chloro.

4. A compound as defined in claim 3 wherein n is 1.

5. The compound as defined in claim 4 which is 2-chloro-6-(2-(2-furanylmethoxy)ethoxy)-4-(trichloromethyl)pyridine.

6. A compound as defined in claim 1 wherein Y is dichloromethyl.

7. A compound as defined in claim 1 wherein Y is dichlorofluoromethyl.

8. A compound as defined in claim 1 wherein X is bromo.

9. A compound as defined in claim 1 wherein X is fluoro.

10. A fungicidal composition comprising a fungicidally effective amount of a compound corresponding to the formula:

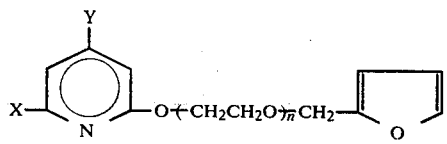

wherein Y represents trichloromethyl, dichloromethyl or dichlorofluoromethyl; X represents chloro, bromo or fluoro and n represents an integer of 1 or 2, in intimate admixture with an inert adjuvant therefor.

11. A composition as defined in claim 10 wherein Y is trichloromethyl.

12. A composition as defined in claim 11 wherein X is chloro.

13. A composition as defined in claim 12 wherein n is 1.

14. The composition as defined in claim 13 wherein the compound is 2-chloro-6-(2-(2-furanylmethoxy)-ethoxy)-4-(trichloromethyl)pyridine.

15. A composition as defined in claim 10 wherein Y is dichloromethyl.

16. A composition as defined in claim 10 wherein Y is dichlorofluoromethyl.

17. A composition as defined in claim 10 wherein X is bromo.

18. A composition as defined in claim 10 wherein X is fluoro.

19. A method for protecting plants from plant fungal disease organisms which attack the plant root system which comprises contacting plants, plant parts or their habitat with a non-phytotoxic, plant protecting amount of a plant protectant corresponding to the formula:

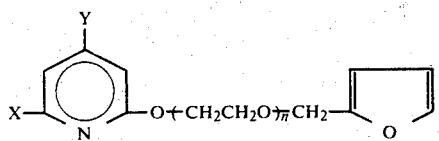

wherein Y represents trichloromethyl, dichloromethyl or dichlorofluoromethyl; x represents chloro, bromo or fluoro and n represents an integer of 1 or 2, in intimate admixture with an inert adjuvant therefor.

20. The method as defined in claim 20 wherein the plants, plant parts or habitat are contacted with the plant protector prior to the plants being attacked by plant root disease organisms.

21. The method as defined in claim 20 wherein the plants, plant parts or habitat are contacted with the plant protector after the plants have been attacked by plant root disease organisms.

22. The method as defined in claim 20 wherein the plant roots are contacted with the plant protectant.

23. The method as defined in claim 20 wherein the above-ground portions of the plants are contacted with the plant protectant.

24. The method as defined in claim 20 wherein plant seeds are contacted with the plant protectant.

25. A method as defined in claim 20 wherein Y is trichloromethyl.

26. A method as defined in claim 25 wherein X is chloro.

27. A method as defined in claim 26 wherein n is 1.

28. The method as defined in claim 27 wherein the plant protectant is 2-chloro-6-(2-(2-furanylmethoxy)-ethoxy)-4-(trichloromethyl)pyridine.

29. A method as defined in claim 20 wherein Y is dichloromethyl.

30. A method as defined in claim 20 wherein Y is dichlorofluoromethyl.

31. A method as defined in claim 20 wherein X is bromo.

32. A method as defined in claim 20 wherein X is fluoro.

* * * * *

UNITED STATES PATENT AND TRADEMARK OFFICE
CERTIFICATE OF CORRECTION

PATENT NO. : 4,360,524
DATED : November 23, 1982
INVENTOR(S) : Howard Johnston

It is certified that error appears in the above—identified patent and that said Letters Patent is hereby corrected as shown below:

In the abstract, line 5, " 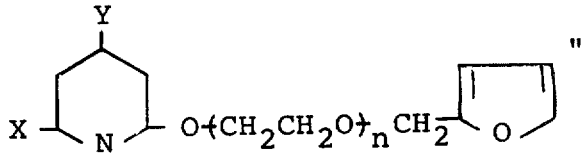 "

should be drawn -- 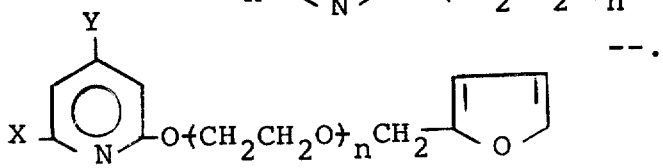 --.

Column 1, line 59, "$-(CH_2)_3OR_2$" should read -- $-(CH_2)_3OR^2$, --.

Column 4, line 12, "for" should read --of--.

Column 13, line 9, the "x" should be changed from a lower case to a capital --X--.

Signed and Sealed this

Fifth Day of April 1983

[SEAL]

Attest:

GERALD J. MOSSINGHOFF

Attesting Officer          Commissioner of Patents and Trademarks